United States Patent
Mann et al.

[11] Patent Number: 5,957,890
[45] Date of Patent: *Sep. 28, 1999

[54] CONSTANT FLOW MEDICATION INFUSION PUMP

[75] Inventors: Alfred E. Mann, Sylmar; Magdi F. Habib, Valencia; Susan M. McConnell, Woodland Hills; William P. Van Antwerp, Valencia; Peter C. Lord, Santa Clarita, all of Calif.

[73] Assignee: MiniMed Inc., Sylmar, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/871,830

[22] Filed: Jun. 9, 1997

[51] Int. Cl.$^6$ .................................................. A61M 37/00
[52] U.S. Cl. ............................................. 604/131; 604/93
[58] Field of Search ............................. 604/93, 131, 133, 604/140, 141, 153, 236, 411, 891.1, 892.1, 51, 65, 139, 201, 204, 237, 246; 137/551, 556; 251/903, 82, 83, 159

[56] References Cited

U.S. PATENT DOCUMENTS

| | | |
|---|---|---|
| 3,840,009 | 10/1974 | Michaels et al. . |
| 4,299,220 | 11/1981 | Dorman . |
| 4,537,680 | 8/1985 | Barth . |
| 4,626,244 | 12/1986 | Reinicke . |
| 4,715,852 | 12/1987 | Reinicke et al. . |
| 4,718,893 | 1/1988 | Dorman et al. . |
| 4,772,263 | 9/1988 | Dorman et al. . |
| 5,009,251 | 4/1991 | Pike et al. . |
| 5,176,641 | 1/1993 | Indriss . |
| 5,176,644 | 1/1993 | Srisathapat et al. . |
| 5,197,322 | 3/1993 | Indravudh . |
| 5,382,236 | 1/1995 | Otto et al. . |
| 5,722,957 | 3/1998 | Steinbach . |

FOREIGN PATENT DOCUMENTS

| | | |
|---|---|---|
| 732113A1 | 3/1996 | Germany . |
| 742025A1 | 5/1996 | Germany . |
| 9634639 | 11/1996 | Germany . |

OTHER PUBLICATIONS

The Esox Catalog 1995; pp. 1–7; Esox Technology Corporation.

*Primary Examiner*—Wynn Wood Coggins
*Assistant Examiner*—Sharon Finkel
*Attorney, Agent, or Firm*—MiniMed Inc.

[57] ABSTRACT

A medication infusion pump is provided for substantially constant flow delivery of a selected medication from a medication chamber through a catheter to a patient. The medication infusion pump comprises a compact housing adapted for implantation into the body of a patient, wherein the housing defines a hollow interior forming a medication chamber. An inlet port on the housing permits transcutaneous access to and filling of the medication chamber within the housing. A flexible propellant reservoir occupies a portion of the medication chamber volume and is filled with a selected fluid propellant to apply a substantially constant pressure to the medication for medication delivery with substantially constant flow through an elongated capillary tube and the catheter for administration to the patient. The capillary tube is spooled within the housing at the perimeter thereof in association with an annular filter of large surface area to prevent impurities and particulate from entering and potentially clogging the capillary tube. The inlet port also includes a click plate for providing a positive feedback indication of proper registration between the inlet port and a refill needle for refilling the medication chamber.

92 Claims, 7 Drawing Sheets

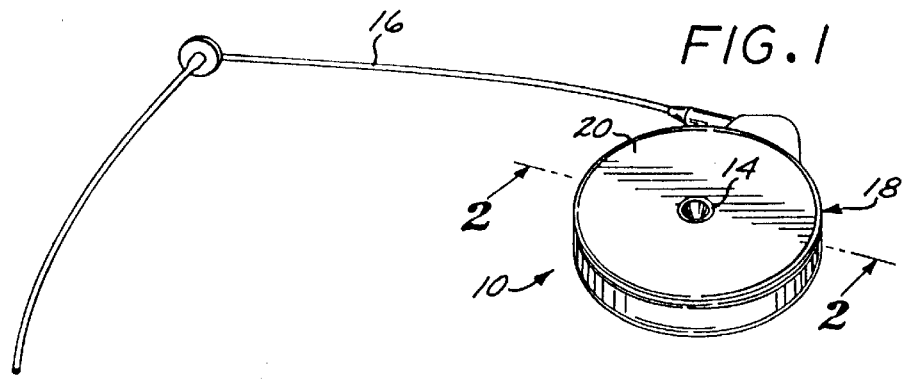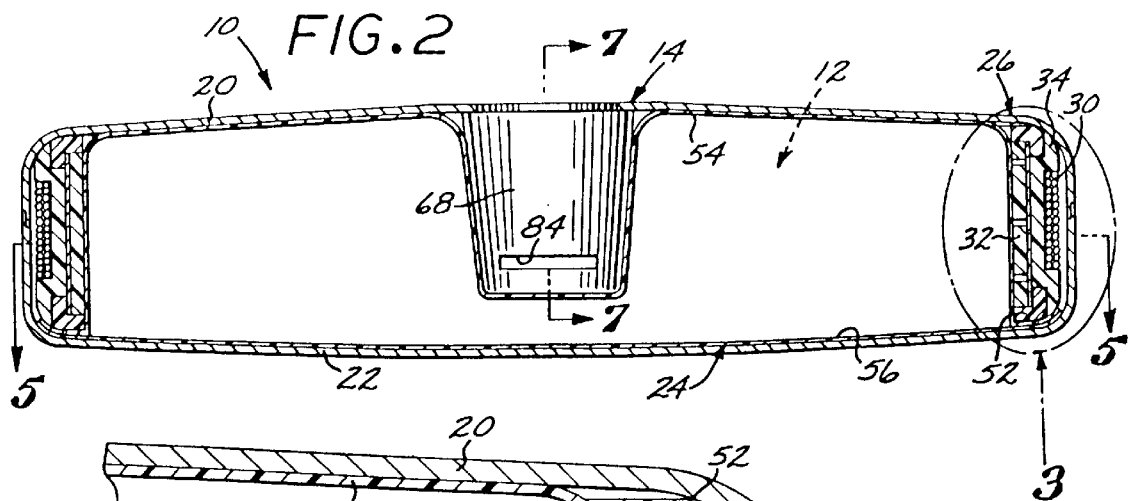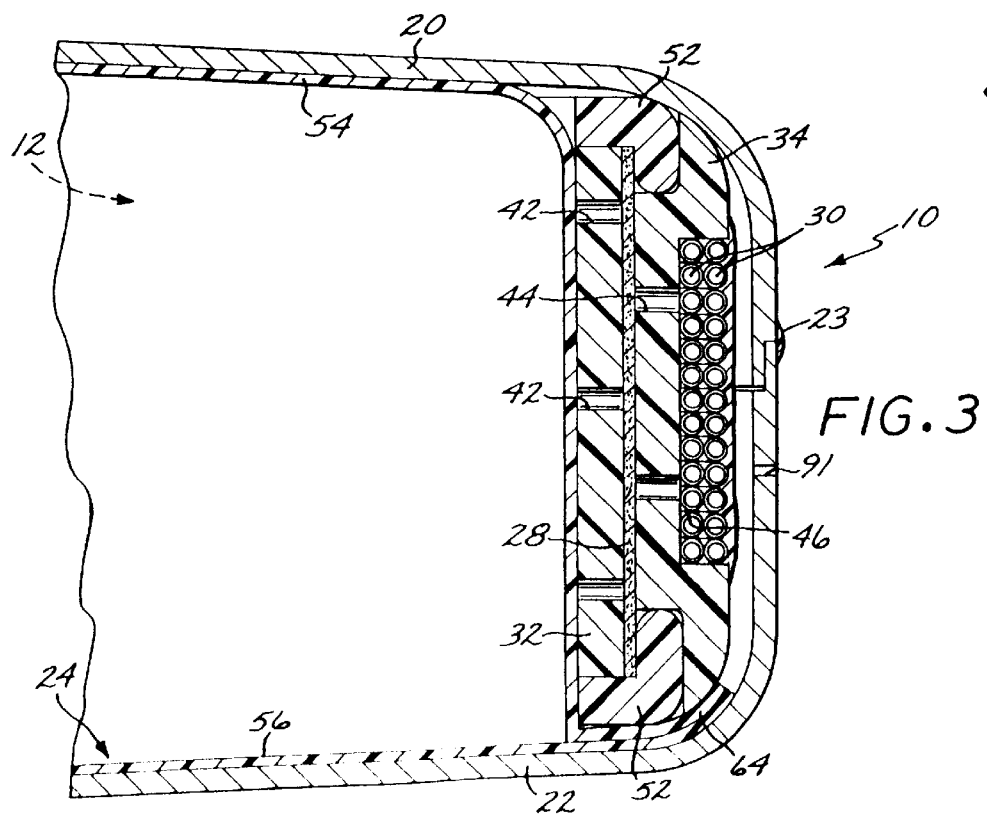

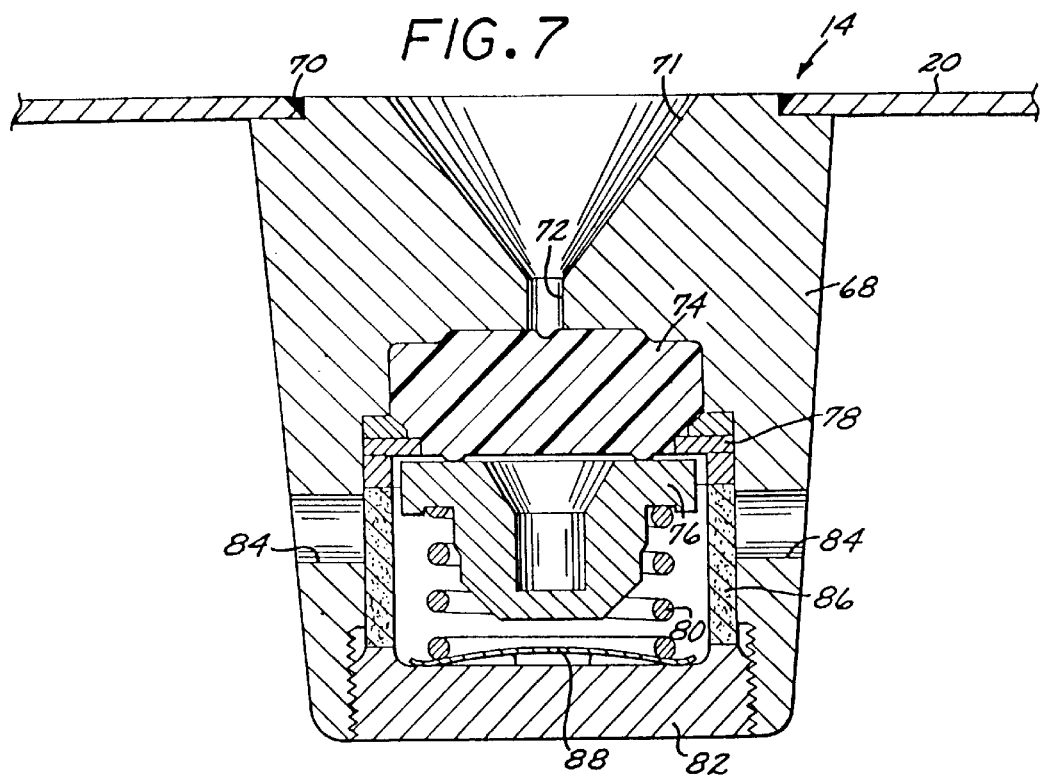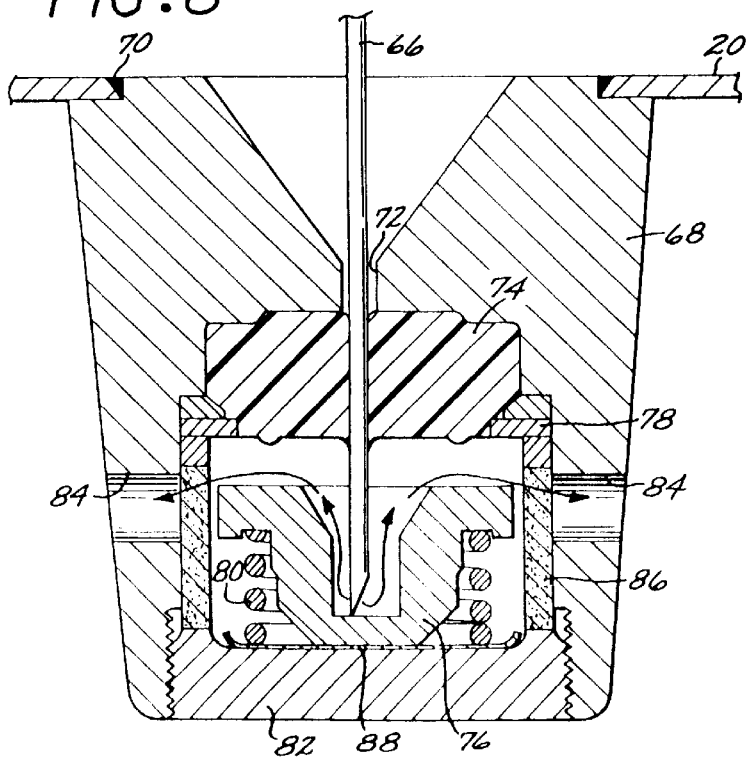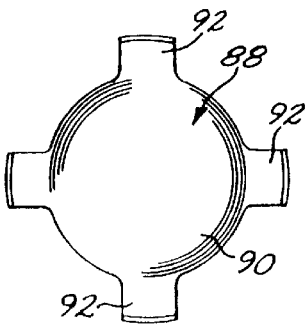

5,957,890

CONSTANT FLOW MEDICATION INFUSION PUMP

BACKGROUND OF THE INVENTION

This invention relates generally to medication infusion pumps for controlled delivery of a selected medication to a patient over an extended period of time. More particularly, this invention relates to an improved medication infusion pump of the constant flow type, for administration of the selected medication to the patient on a substantially constant flow basis. In the preferred form, the medication infusion pump of the present invention is adapted for implantation directly into the body of the patient, and for periodic transcutaneous refilling of a medication chamber within the pump.

Medication infusion pumps are generally known in the art for use in delivering a selected medication to a patient including humans and other animals in accordance with an administration schedule which can be preselected or, in some instances, preprogrammed. In recent years, such infusion pumps have been developed in compact form adapted for direct implantation into the body of a patient, to deliver a specific medication such as insulin to the patient in controlled doses over an extended period of time. An implantable infusion pump of this general type includes an internal medication chamber for receiving and storing a supply of the selected medication in liquid form. In some forms, the medication is delivered from the medication chamber into the body of the patient by a miniature pump operated by associated programmable control means for delivering the medication to the patient in selected doses at selected times. For one example of a medication infusion pump of this type, see U.S. Pat. No. 4,573,994 (Fischell). In other designs, the medication is maintained within the medication chamber defined by a metal bellows under a positive pressure for delivery as a substantially continuous and preferably constant flow through an appropriate restriction such as a capillary tube. For examples of infusion pumps which use such a positive pressure system with a capillary tube for continuous flow delivery of medication, see U.S. Pat. Nos. 3,731,681 (Blackshear), and 3,951,147 (Tucker).

The present invention is directed to an improved implantable flow infusion pump of the constant flow type, wherein the pump components are arranged and assembled in a highly compact geometry that is compatible with cost-efficient manufacture, and which further provides accurate and reliable delivery of the medication over an extended period of time. The improved infusion pump is particularly designed to provide a substantially optimized and low profile housing configuration suited for implantation into the patient. Moreover, the pump incorporates an improved capillary tube and related mounting arrangement in association with a filter of substantially maximized surface area, to result in a capillary tube and filter package that resists clogging. Such resistance to clogging is especially significant when the pump is used to deliver complex protein-based medications, such as insulin, which tend to develop particulate aggregates along fluid flow paths.

SUMMARY OF THE INVENTION

In accordance with the invention, an improved medication infusion pump is provided for substantially constant flow delivery of a selected medication to a patient. The infusion pump comprises a compact housing adapted for implantation directly into the body of a patient including humans and other animals, and includes an inlet port to accommodate transcutaneous filling and refilling of a medication chamber within the housing. The medication chamber is subjected to a predetermined and substantially constant pressure by means of a flexible propellant reservoir. The propellant reservoir contains a selected fluid propellant which applies a predetermined pressure to the medication for discharge flow of the medication through a filter of relatively large surface area and a porous restrictive element such as an elongated capillary tube which meters the medication flow to and through an outlet catheter to the patient.

In the preferred form of the invention, the compact housing comprises a pair of shell-shaped housing elements adapted for assembly and interconnection as by a single weld to define a hollow housing interior. The inlet port is mounted on one of the housing elements and communicates with the housing interior which forms the medication chamber occupying substantially the entire housing internal volume. The flexible propellant reservoir comprises a sealed bag mounted directly within the medication chamber and contains the selected fluid propellant having a vapor pressure so that the propellant is present in a mixed liquid-vapor state to apply a predetermined positive pressure to the medication within the housing. Alternately, the medication chamber may be defined by the flexible bag and the propellant reservoir defined by the residual internal volume of the housing. A bobbin assembly, including the filter and capillary tube, is mounted within the housing at the perimeter thereof, and regulates medication flow from the medication chamber through the filter and capillary tube to the outlet catheter mounted by an outlet port fitting onto the pump housing.

The bobbin assembly comprises a pair of coaxially interfitting bobbin rings assembled in concentric relation, with the filter of annular shape interposed therebetween. An inner bobbin ring is perforated to permit passage of the medication into flow communication with the filter. An outer bobbin ring includes an outlet flow port to which one end of the capillary tube is secured. Accordingly, medication passing through the filter flows through the outlet port for subsequent passage through the capillary tube. The capillary tube is formed preferably from a plastic coated glass tubing with a selected inner diameter size of about 2–10 mils and a length on the order of about 2–750 feet. The capillary tube is wrapped or spooled about the outer bobbin ring, and has the opposite end thereof secured by means of a resilient adapter sleeve to an outlet tube connected in turn via the outlet port fitting to the catheter.

The inlet port, in accordance with a preferred construction, includes a resilient septum adapted for piercing by a refill needle device to permit filling and refilling of the medication chamber. Below the septum, the inlet port includes an inlet valve member normally retained in a closed position but adapted for engagement by the tip of the refill needle device for movement to an open position to permit filling of the medication chamber. An over-center click plate is positioned within the inlet port beneath the inlet valve member for depression when the inlet valve member is opened by the refill needle device. Depression of the click plate is associated with a distinct click that can be detected as an audible and/or tactile feedback to indicate correct engagement and registration between the refill needle device and the inlet port.

As the medication is delivered through the inlet port to fill the medication chamber, the propellant reservoir collapses to a substantially minimal volume, whereby substantially the entire internal volume of the housing is occupied by the medication. This results in an infusion pump construction that has substantially maximized medication capacity with a highly compact pump housing size and shape. Moreover, this construction allows greater freedom as to the shape of the pump housing to include contoured shapes which would be more physiologically and cosmetically suited for patient implantation. As the medication is delivered over time to the patient through the filter and the capillary tube and catheter, the propellant reservoir gradually expands while maintaining the medication under the predetermined constant positive pressure.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view illustrating a medication infusion pump embodying the novel features of the invention;

FIG. 2 is an enlarged transverse vertical sectional view taken generally on the line 2—2 of FIG. 1, and depicting a medication chamber in a substantially empty condition;

FIG. 3 is a further enlarged fragmented sectional view corresponding generally to the encircled region 3 of FIG. 2;

FIG. 7 is an enlarged fragmented vertical sectional view taken generally on the line 7—7 of FIG. 2, and showing construction details of a preferred inlet port for the pump;

FIG. 8 is a fragmented vertical sectional view similar to FIG. 7, and depicting the inlet port in an open condition;

FIG. 9 is a top plan view of a click plate for use in the inlet port shown in FIGS. 7 and 8;

DETAILED DESCRIPTION OF THE PREFERRED EMBODIMENT

Figure 4:
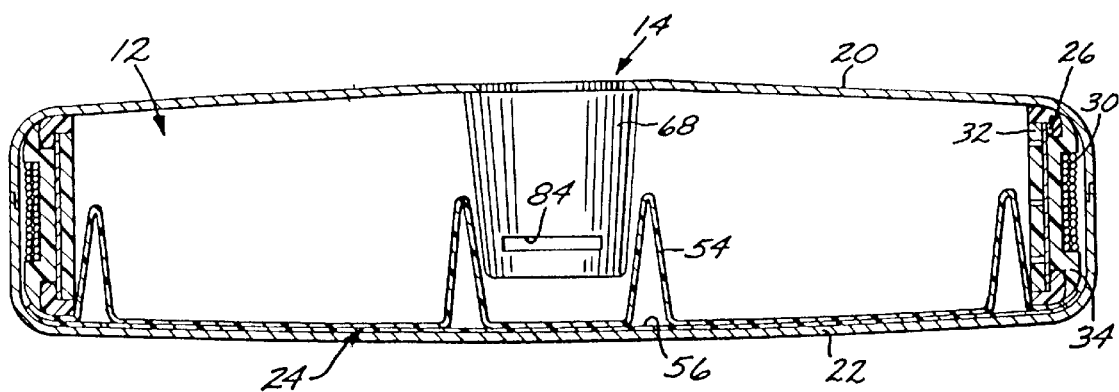
FIG. 4 is an enlarged transverse vertical sectional view similar to FIG. 2, but depicting the medication chamber in a substantially filled condition.

As shown in the exemplary drawings, a medication infusion pump referred to generally in FIG. 1 by the reference numeral 10 is provided for use in administering a selected medication to a patient with a substantially constant flow rate over an extended period of time. The infusion pump includes an internal medication chamber 12 (FIG. 4) for receiving and storing a supply of the selected medication, wherein this medication chamber is adapted to be refilled at appropriate intervals by means of an inlet port 14. The pump 10 is particularly designed for direct implantation into the body of a patient, and includes an improved capillary tube and filter arrangement for delivering the medication from the chamber 12 through an outlet catheter 16 to the patient at a selected internal administration site. The pump 10 is constructed to provide a substantially optimized medication storage volume in a highly compact and low profile configuration that is designed for cost-efficient assembly and reliable long-term operation.

The illustrative medication infusion pump 10 comprises a small and substantially self-contained unit for direct implantation in the body of a patient, wherein the term "patient" will be understood to include humans and other animals. The pump 10 comprises a hermetically sealed pump housing 18 made from a biocompatible material such as titanium or titanium alloy. In the preferred form, the housing 18 includes a pair of interfitting upper and lower shell-shaped housing elements 20 and 22 which are assembled in face-to-face relation to define a hollow housing interior of generally disk-shape having a selected narrow height which can be very small, for example, even as thin as less than about 0.1 inch. The diameter can be of almost any reasonable size, for example, on the order of 1–3 inches. It will be noted, however, that the illustrative disk-shaped housing 18 can be constructed with almost any shape and need not be round or of narrow height. As shown best in FIGS. 2 and 3, these housing elements 20 and 22 include peripheral rims shaped for mating engagement, such as by coining the rim of the lower housing element 22 to accommodate reception of the rim of the upper housing element 20. When assembled, the two housing elements 20 and 22 are secured together in a hermetically sealed manner, as by means of a single weld 23, without requiring a separate weld ring insert to position and interconnect the housing components, and further without requiring multiple weld steps associated with a separate weld ring insert. The resultant disk-shaped housing 18 has a compact and low profile circular construction suited for direct implantation into the body of a patient. Alternative compact housing shapes may be used, particularly with respect to contouring the housing for a more optimum physiological and/or cosmetic shape when implanted into the body of a patient.

In general terms, the pump housing 18 defines a hollow interior volume occupied substantially and predominantly by the medication chamber 12. A related propellant reservoir 24 is incorporated directly within the medication chamber 12 and functions as will be described in more detail to apply a predetermined positive pressure to the medication. The medication chamber 12 is disposed in flow communication with the inlet port 14 shown located centrally in the upper housing element 20 for receiving the supply of medication therein. The medication chamber 12 is also disposed in flow communication with a bobbin assembly 26 which in this embodiment is mounted within the housing 18 at the perimeter thereof. The bobbin assembly 26 includes a filter 28 of large surface area for filtering the medication as it flows to and through a flow restrictive element such as an elongated capillary tube 30 coiled within the housing. The capillary tube 30 provides a known restriction to fluid flow, and cooperates with a selected propellant within the propellant reservoir 24 to insure substantially constant flow of the medication through the capillary tube and the outlet catheter 16 to the patient. As the medication in the medication chamber 12 is delivered to the patient, the propellant reservoir 24 expands in volumetric size to maintain the medication under selected and substantially constant pressure.

Figure 5:
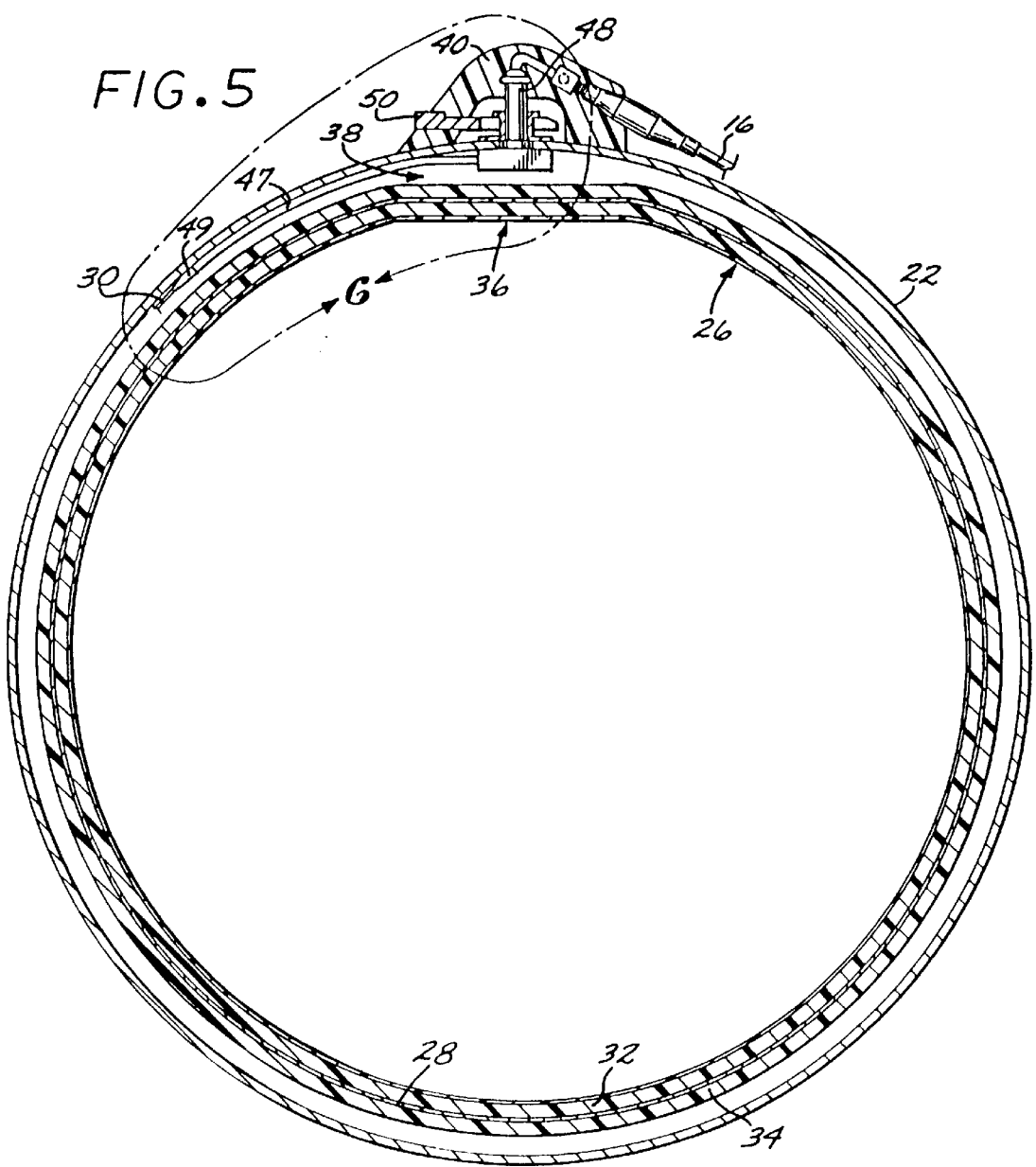
FIG. 5 is a horizontal sectional view taken generally on the line 5—5 of FIG. 2.
Figure 13:
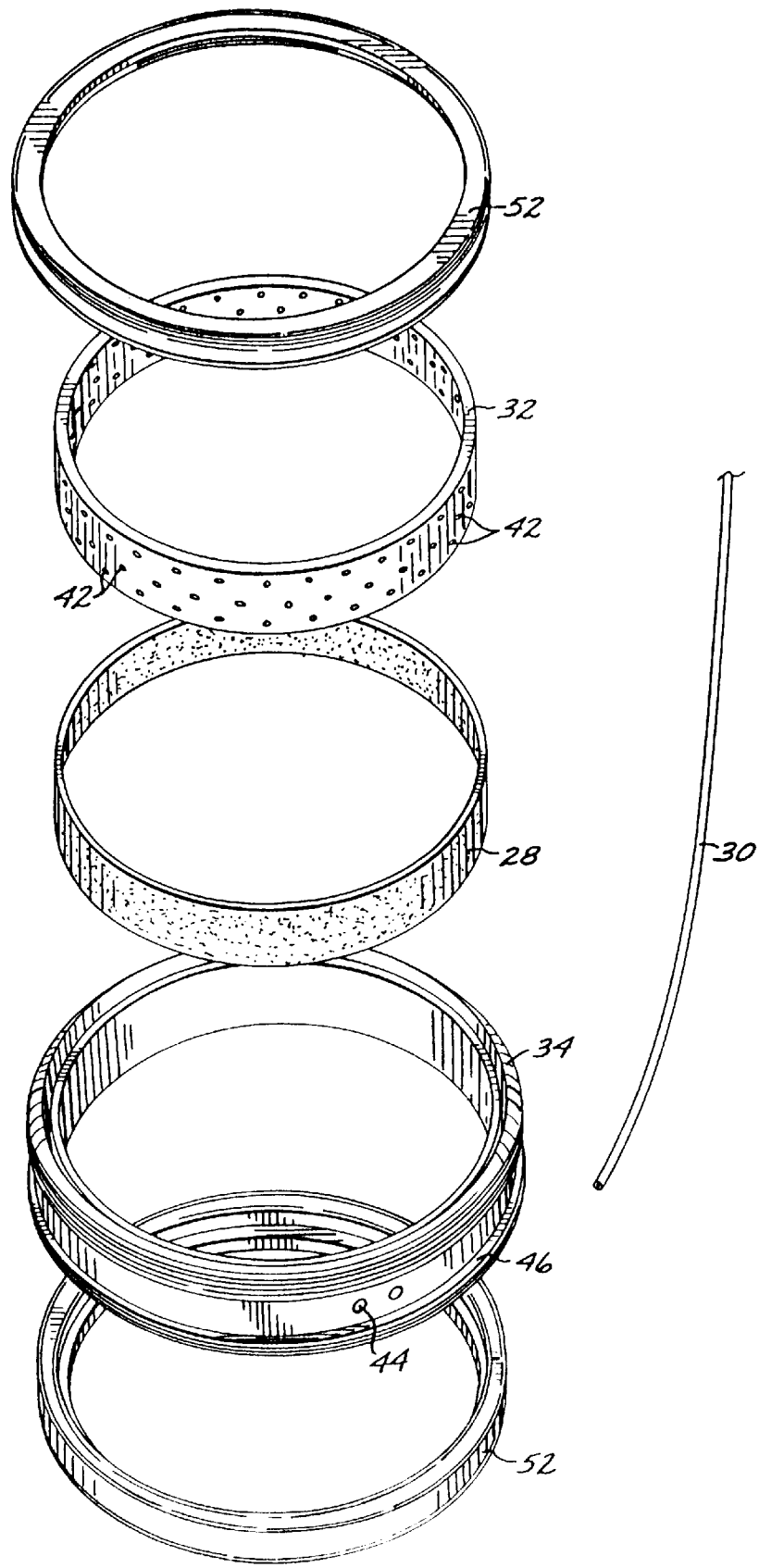
FIG. 13 is an exploded perspective view illustrating components of a bobbin assembly for use in the invention.

The bobbin assembly 26 is shown in more detail in FIGS. 3, 4, and 13. As shown, the bobbin assembly 26 comprises a generally annular inner bobbin ring 32 adapted for concentric assembly with a generally annular outer bobbin ring 34, with the filter 28 of annular shape disposed therebetween in a press-fit manner. The assembled bobbin rings 32 and 34 have a diametric size and shape to fit relatively closely with a simple drop-in slide fit into the perimeter of the housing 18, thereby to permit the substantial majority of the housing internal volume to be occupied by the medication chamber 12 with the related propellant reservoir 24 therein. The bobbin rings 32 and 34 desirably include small flats as indicated by arrow 36 in FIG. 5 to insure assembly thereof in a predetermined rotational alignment, and further to provide a small clearance zone indicated by arrow 38 to accommodate mounting of a side outlet port fitting 40 for connection of the capillary tube 30 to the outlet catheter 16, as will be described in more detail.

The inner bobbin ring 32 has a plurality of small perforations 42 formed therein for flow passage of the medication from the medication chamber 12 to and through the filter 28. The filter 28 is provided to remove contaminants and particulate from the liquid medication, wherein such constituents could otherwise obstruct and clog the capillary tube 30 to interfere with proper operation of the infusion pump. While a variety of different filter materials can be used, one preferred filter material is polyethersulfone capable of filtering particles of about 0.2 micron in size. In the preferred construction, the filter 28 is secured to the inner bobbin ring 32 in any suitable manner as by heat staking a small surface thereof in the vicinity of the flat 36 (FIG. 4) to the inner bobbin ring. Alternately, the filter 28 may be physically captured between the inner and outer bobbin rings.

Figure 6:
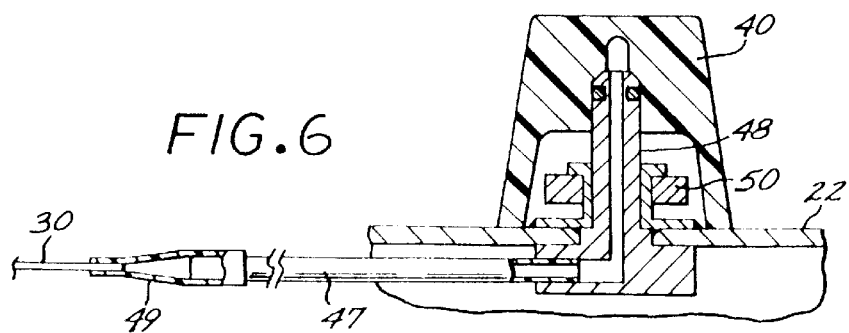
FIG. 6 is an enlarged fragmented and partially developed sectional view corresponding generally to the encircled region 6 of FIG. 5.

The outer bobbin ring 34 has an outlet port 44 formed therein for reception of one end of the capillary tube 30, as shown in FIG. 3. The outer surface of the outer bobbin ring 34 defines a shallow recess 46 to accommodate spooled wraparound reception of a selected length of the capillary tube 30. An opposite end of the capillary tube 30 is then coupled to a larger diameter outlet tube 47 (FIG. 6) by means of a tapered resilient adapter sleeve 49 of a silicone elastomer or the like for press-fit reception and retention of aligned adjacent tubing ends. The outlet tube 47 is connected in turn to the side outlet port fitting 40, shown in FIGS. 5 and 6 in the form of a small port tube 48 and related clip-on connector 50 of the general type shown and described in U.S. Pat. No. 5,527,307 (Srisathapat), which is incorporated by reference herein. The outer bobbin ring 34, with the capillary tube 30 assembled therewith, is assembled with the inner bobbin ring 32 and filter 28 to form a compact ring-shaped subassembly to slide-fit closely within the perimeter of the housing interior. A pair of gasket seals 52 are fitted between the bobbin rings 32 and 34 at the top and bottom thereof, to minimize undesired pockets of medication by confining medication within the bobbin assembly for flow through the filter 28 and capillary tube 30.

The diametric size and overall length of the capillary tube 30 is selected, in combination with the design of the propellant reservoir 24 and a fluid propellant therein, to yield a desired and substantially constant flow rate of the medication to the patient. In this regard, while different capillary tube sizes and lengths may be used for different applications, one preferred tube construction for delivery of medication and other therapeutic agents has an inner diameter of about 2–10 mils, and an overall length of about 2–750 feet, with a more preferred construction having an inner diameter of about 3–5 mils and a length of about 40–200 feet. One such capillary tube comprises a polyimide coated glass tubing. This capillary tubing is particularly suited for use in the bobbin assembly of the present invention which mounts at the perimeter of the pump housing 18 where the glass-based tubing is not subjected to sharp bends. A quantity of epoxy 51 (FIG. 3) or the like may be used to encase and sealingly retain the capillary tube 30 within the bobbin ring recess 46.

Figure 10:
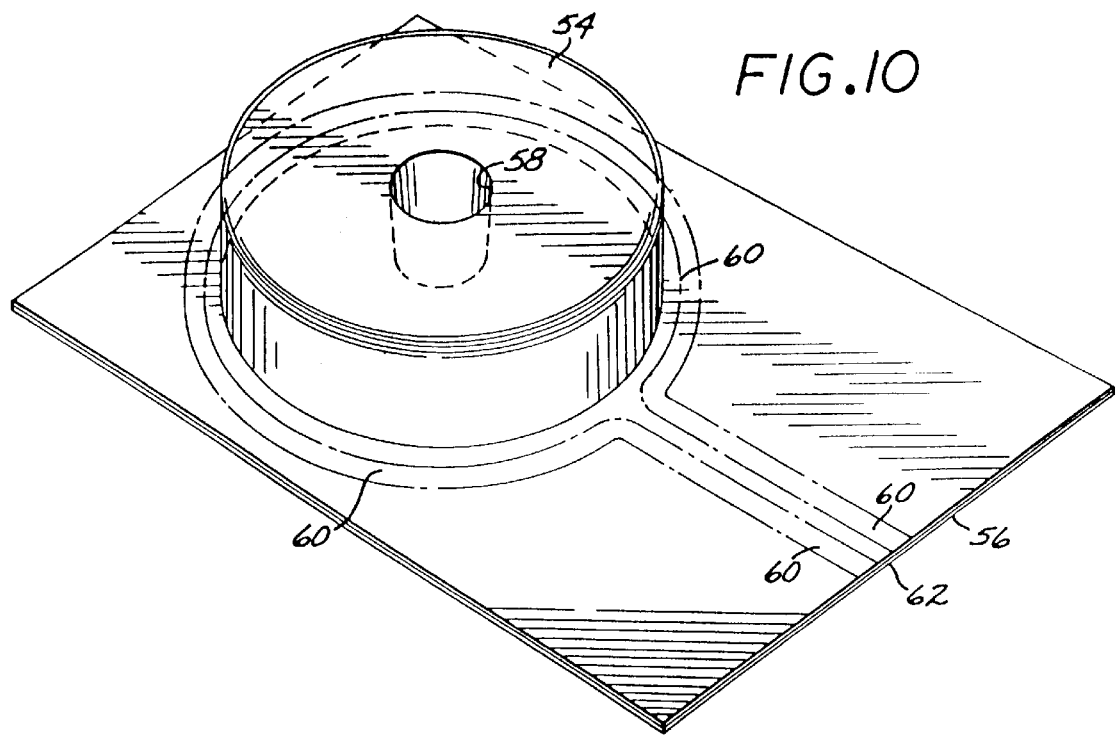
FIG. 10 is a perspective view showing a propellant reservoir in a partially manufactured state, for use in the infusion pump of the invention.
Figure 11:
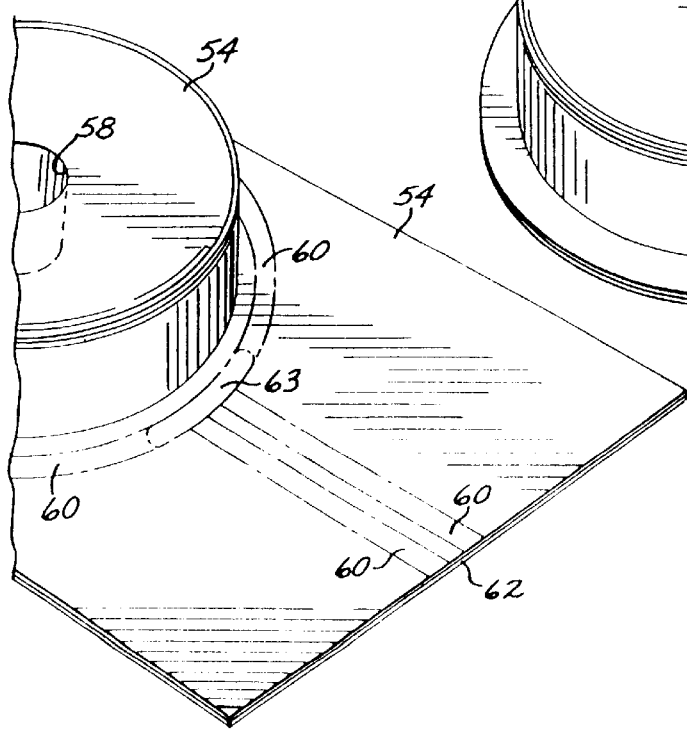
FIG. 11 is a fragmented perspective view depicting further manufacture of the propellant reservoir.
Figure 12:
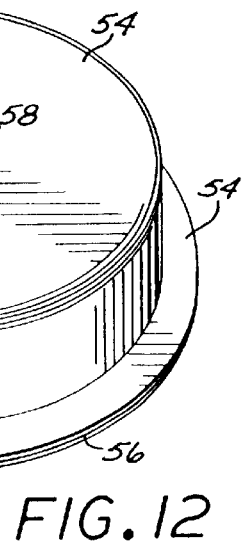
FIG. 12 is a perspective view of the completed propellant reservoir.

The propellant reservoir 24 is mounted directly within the medication chamber 12 within the pump housing 18. In this regard, the exemplary drawings show the propellant reservoir 24 in a preferred form, constructed as a sealed flexible or resilient bag mounted within the housing 18 so that the reservoir bag can act directly upon and apply pressure to the medication. FIGS. 10–12 show the propellant reservoir bag constructed from a pair of overlying sheets 54 and 56 of flexible plastic film material such as urethane or a selected fluoropolymer sheet or the like chosen for compatibility with the medication to be dispensed. Alternately, the plastic film material may be a sandwich or laminant, or may include a metal sputtered coating, or may be substituted by a metal film material. Other coating formulations such as an organic oxide coating may also be used for the plastic film material to minimize or prevent diffusion therethrough of the fluid propellant. As shown in the illustrative drawings, the upper sheet 54 is formed generally as an inverted cup and also includes a central depression 58 to accommodate the pump inlet port 14 when installed into the pump housing. The overlying sheets 54 and 56 are sealed together as by a heat seam or weld 60, initially leaving a narrow fill port 62 open to permit filling of the bag interior with the selected fluid propellant. After filling, the fill port 62 is also closed and sealed as indicated at 63 (FIG. 11) and the sheet margins trimmed to create a short outwardly projecting flange 64 (FIG. 12). The filled reservoir 24 is then installed into the housing with a simple drop-in slide fit, and the subsequently installed bobbin assembly 26 overlies and retains the bag flange 64 thereby retaining the propellant reservoir in place within the pump housing.

The fluid propellant within the propellant reservoir 24 is selected to apply a substantially constant and predetermined positive pressure to the medication within the medication chamber 12, regardless of the quantity of medication remaining within the chamber 12. While various propellants are available for this purpose, freon compounds are available in a range of vapor pressures designed to provide a predetermined and substantially constant pressure to the medication contained within the medication chamber. It will be understood, however, that other liquid-vapor volatile fluids can be used. In a typical application, a mixed state liquid-vapor fluid designed to provide a positive pressure of about 5–50 psi, and preferably about 23–24 psi, at normal body temperature is used.

FIGS. 7–9 show the inlet port 14 in more detail, to include means for positively indicating proper engagement between a refill needle 66 (FIG. 8) and the inlet port. This feature is particularly desirable since the infusion pump 10 is refilled transcutaneously, such that the inlet port 14 must be located by palpation through the skin of the patient. By providing a feedback indication of proper engagement between the refill needle 66 and the inlet port 14, correct delivery of the refill medication to the medication chamber 12 is assured, and incorrect delivery of the medication directly from the refill needle 66 to the patient is prevented. This feature is especially desirable in a positive pressure medication reservoir device since the refill medication must be delivered under pressure to the medication chamber.

The inlet port 14 comprises a port or valve body 68 adapted for mounting as by welding onto the upper housing element 20 in alignment with a central opening 70. The body 68 defines a conical recess 71 for guided reception of the tip of the refill needle to a narrow access port 72, the lower end of which is closed by a resilient self-sealing septum 74. A cup-shaped valve member 76 is mounted below the septum 74 and is normally retained in sealed contact with a lower surface of the septum and with an annular valve seat 78 by means of a spring 80 reacting between the valve member 76 and a plug 82 threaded into the bottom of the port body 68. When the valve member 76 is engaged by the tip of the refill needle 66 (FIG. 8), the valve member is displaced downwardly from the septum 74 and valve seat 78 to open a flow path through side slots 84 in the port body 68 leading to the medication chamber 12. An annular filter element 86 may be provided along this flow path to filter out any particulate in the refill medication. Withdrawal of the refill needle 66 from the inlet port 14 is accompanied by spring-loaded return movement of the valve member 76 to the initial closed position. The threaded advancement of the plug 82 into the port body 68 can variably select and adjust the spring force urging the valve member 76 to the closed position. The plug 82 may conveniently be secured to or otherwise formed as a one-piece component with the annular filter element 86, whereby the combined plug and filter retain the valve seat 78 in place. Importantly, the valve member 76 combines with the septum 74 to provide a redundant closure at the inlet port side of the medication chamber 12.

In accordance with one aspect of the invention, an overcenter click plate 88 is mounted between the valve member 76 and the plug 82, in a position for depression by the valve member 76 as it moves to the open position. FIG. 9 shows the click plate 88 in a preferred form to include an upwardly convex dome element 90 supported on four perimeter feet 92. Depression of the click plate 88 results in an audible click sound that can also be felt as a tactile feedback by the person holding the refill needle 66. Thus, the click plate 88 provides a feedback indication, audible and/or tactile, to positively indicate that the refill needle 66 is properly engaged and registered with the inlet port 14.

Figure 14:
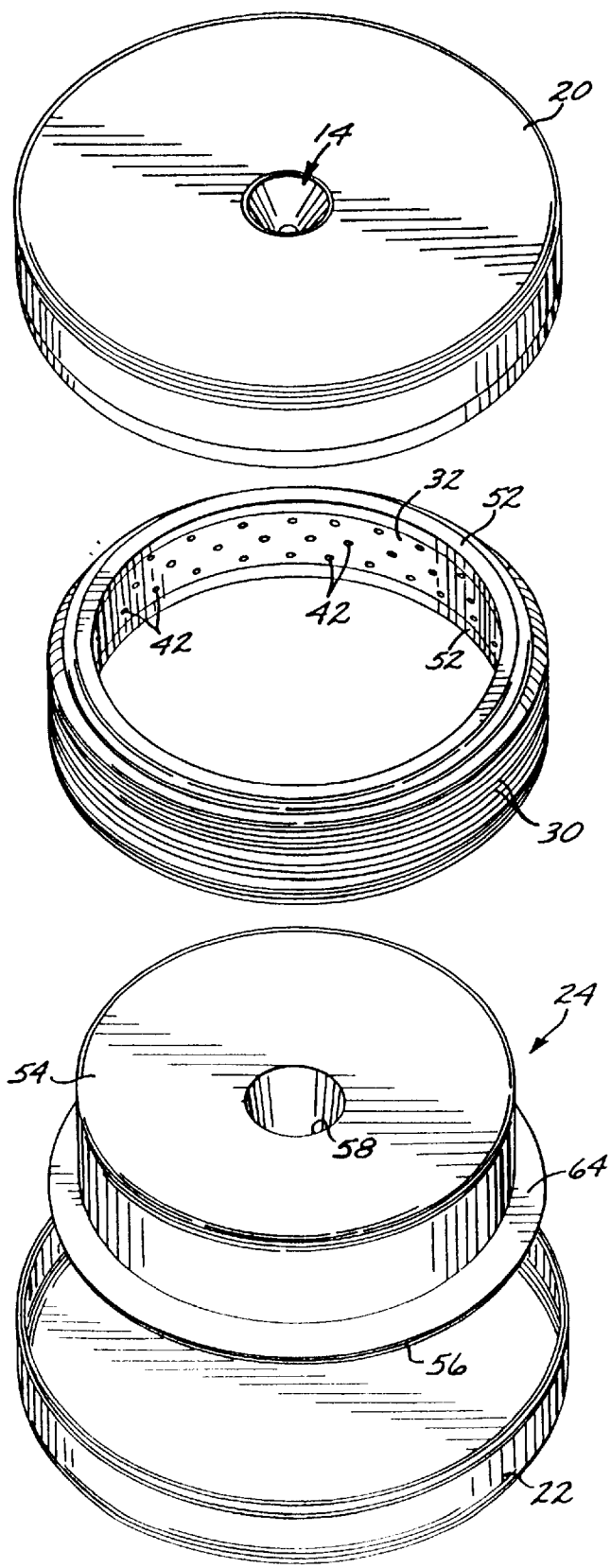
FIG. 14 is an exploded perspective showing installation of the bobbin assembly and propellant reservoir into a housing to form the infusion pump of the present invention.

FIG. 14 shows the assembly of the infusion pump components, including the major subassemblies thereof to form the constant flow infusion pump 10 of the present invention. As shown, the assembled propellant reservoir 24 filled with the selected fluid propellant is dropped with a slide fit into the lower housing element 22. The bobbin assembly 26 is then dropped with a slide fit into the lower housing element 22, in surrounding relation to the propellant reservoir 24, with the outer end of the capillary tube 30 appropriately connected to the side outlet port fitting 40 (not shown in FIG. 14). The upper housing element 20, with the inlet port 14 preassembled therewith, is then placed onto the lower housing element 22, and these housing elements 20, 22 are hermetically secured to form the infusion pump. In the assembled state, the gasket seals 52 (FIG. 3) on the bobbin assembly 26 engage the upper and lower housing elements 20, 22. In a preferred configuration, a small port 91 may be provided in one of the housing elements 20, 22, as shown in FIG. 3 with respect to the lower housing element 22, to permit post-assembly hermetic testing of the pump. This port 91 may also be used to permit post-assembly introduction of the epoxy 51 (FIG. 3) to retain the capillary tube 30 and further to fill and occupy the residual space between the bobbin assembly 26 and the inside perimeter surface of the housing 18. This port 91 can then be closed and sealed as by welding.

In operation, filling of the medication chamber 12 with the selected medication is accompanied by appropriate volumetric collapse of the propellant reservoir 24 to accommodate the medication, as shown in FIG. 4. This collapse of the propellant reservoir enables substantially the entire internal volume of the housing, extending throughout the width and height thereof, to be filled with the medication, thereby resulting in a substantially maximized medication capacity relative to the pump housing size. The propellant reservoir and the fluid propellant therein exert the desired substantially constant pressure on the medication to deliver the medication at a substantially constant flow rate through the filter 28 and capillary tube 30 and catheter 16 to the patient. Such medication delivery is accompanied, of course, by gradual increase in the volumetric size of the propellant reservoir as the medication is dispensed. When the medication is entirely dispensed from the pump, the propellant reservoir 24 expands to conform to the shape of and to substantially entirely fill the medication chamber 12.

A variety of further modifications and improvements to the medication infusion pump of the present invention will be apparent to those persons skilled in the art. As one example, it will be recognized and understood by persons skilled in the art that the pump can be modified to place the medication within the flexible bag and the propellant within the residual internal volume of the pump housing, with appropriate mounting of the flexible bag in flow communication with the inlet port 14 and the capillary tube 30. Accordingly, no limitation on the invention is intended by way of the foregoing description and accompanying drawings, except as set forth in the appended claims.

What is claimed is:

1. A medication infusion pump, comprising:
   a housing formed to define a hollow housing interior, said hollow housing interior forming a medication chamber for receiving a selected medication;
   an inlet port mounted on said housing and adapted for removable reception of a refill needle to permit delivery of the medication into said medication chamber;
   a propellant reservoir positioned within said medication chamber, said propellant reservoir comprising a sealed flexible bag with a selected fluid propellant therein to apply a predetermined positive pressure to medication within said medication chamber;
   a flow restrictive element, said flow restrictive element having a first end in flow communication with medication within said medication chamber; and
   an outlet port fitting being coupled in flow communication with a second end of said flow restrictive element for substantially constant delivery of medication passing through said flow restrictive element to a patient,
   wherein the sealed flexible bag is formed from an upper flexible sheet of material connected to a lower sheet, wherein the sealed flexible bag has a size and shape to conform and substantially entirely fill the medication chamber in the absence of medication within the medication chamber, and wherein the upper flexible sheet of the sealed flexible bag progressively collapses to a reduced volumetric size upon introduction of medication into the medication chamber to a substantially minimum volumetric size permitting substantially all of the medication chamber to be filled with medication.

2. The medication infusion pump of claim 1, further including a catheter connected to said outlet port fitting such that the medication passing through said outlet port fitting flows through said catheter to the patient.

3. The medication infusion pump of claim 1 wherein said flow restrictive element comprises an elongated capillary tube.

4. The medication infusion pump of claim 3 wherein said elongated capillary tube is coiled within said housing interior.

5. The medication infusion pump of claim 4 wherein said capillary tube comprises a glass-based capillary tube.

6. The medication infusion pump of claim 5 wherein said capillary tube comprises a plastic coated glass capillary tube.

7. The medication infusion pump of claim 3 wherein said capillary tube is coiled generally at the perimeter of said housing.

8. The medication infusion pump of claim 3 wherein said capillary tube has an inner diameter size of about 2–10 mils, and a length of about 2–750 feet.

9. The medication infusion pump of claim 3 wherein said capillary tube has an inner diameter size of about 3–5 mils, and a length of about 40–200 feet.

10. The medication infusion pump of claim 3 further including a filter mounted at said first end of said capillary tube for filtering medication flowing into said capillary tube from said medication chamber.

11. The medication infusion pump of claim 3, further including a mounting that secures said capillary tube generally at the perimeter of said housing interior.

12. The medication infusion pump of claim 11, wherein said mounting further includes a filter mounted at said first end of said capillary tube for filtering medication flowing into said capillary tube from said medication chamber.

13. The medication chamber of claim 12, wherein said mounting directs medication flow from said medication chamber through said filter and into said capillary tube.

14. The medication chamber of claim 13 wherein said filter has a generally annular shape to extend generally about the perimeter of said housing interior and oriented for radially outward flow passage of medication through said filter and into said first end of said capillary tube.

15. The medication infusion pump of claim 1 wherein said medication chamber occupies substantially all of said housing interior.

16. The medication infusion pump of claim 1 wherein said medication chamber extends substantially without interruption throughout the span and height of said housing interior.

17. The medication infusion pump of claim 1 wherein said selected fluid propellant is a mixed liquid-vapor phase fluid at normal body temperature and ambient pressure conditions to apply said predetermined pressure to the medication within said medication chamber.

18. The medication infusion pump of claim 17 wherein said positive pressure is between about 5–50 psi.

19. The medication infusion pump of claim 17 wherein said positive pressure is about 23–24 psi.

20. The medication infusion pump of claim 1 wherein said housing comprises first and second housing elements assembled in face-to-face relation and including interfitting peripheral rims adapted for hermetic sealed interconnection by a single weld.

21. The medication infusion pump of claim 1 wherein said sealed flexible bag comprises flexible plastic film material.

22. The medication infusion pump of claim 21 wherein said plastic film material includes a metal coating.

23. The medication infusion pump of claim 1 wherein said sealed flexible bag comprises a metal foil material.

24. The medication infusion pump of claim 1 wherein said sealed flexible bag comprises a flexible laminant.

25. The medication infusion pump of claim 3 wherein said outlet port fitting includes a metal outlet tube, and a resilient adapter sleeve for sliding press-fit connection of said metal outlet tube with said second end of said capillary tube.

26. The medication infusion pump in accordance with claim 1, wherein the flow restrictive element is a passive flow restrictive element.

27. A medication infusion pump, comprising:
    a housing formed to define a hollow housing interior, said hollow housing interior forming a medication chamber for receiving a selected medication;
    an inlet port mounted on said housing and adapted for removable reception of a refill needle to permit delivery of the medication into said medication chamber;
    a propellant reservoir positioned within said medication chamber, said propellant reservoir comprising a sealed flexible bag with a selected fluid propellant therein to apply a predetermined positive pressure to medication within said medication chamber;
    a flow restrictive element, said flow restrictive element having a first end in flow communication with medication within said medication chamber, wherein said flow restrictive element comprises an elongated capillary tube;
    an outlet port fitting being coupled in flow communication with a second end of said flow restrictive element for delivering medication passing through said flow restrictive element to a patient; and
    a bobbin assembly mounted within said housing generally at the perimeter thereof, said bobbin assembly including an annular filter element extending generally around the perimeter of said medication chamber for radial outward flow passage of medication through said filter element to said capillary tube.

28. The medication infusion pump of claim 27 wherein said bobbin assembly comprises a perforated inner bobbin ring and an outer bobbin ring assembled in generally concentric relation with said annular filter element disposed therebetween, said outer bobbin ring having a flow port formed therein with said one end of said capillary tube connected thereto.

29. The medication infusion pump of claim 28 wherein said outer bobbin ring further includes an outer surface defining a shallow circumferential recess for spooled reception of said capillary tube therein.

30. The medication infusion pump of claim 28, wherein said bobbin assembly further includes a seal for preventing bypass flow of medication around said filter element.

31. The medication infusion pump of claim 28, wherein said propellant reservoir has an outwardly extending flange formed thereon, said flange being disposed between said bobbin assembly and housing such that said bobbin assembly retains said propellant reservoir in place within said medication chamber.

32. A medication infusion pump, comprising:
    a housing formed to define a hollow housing interior, said hollow housing interior forming a medication chamber for receiving a selected medication;
    an inlet port mounted on said housing and adapted for removable reception of a refill needle to permit delivery of the medication into said medication chamber;
    a propellant reservoir positioned within said medication chamber, said propellant reservoir comprising a sealed flexible bag with a selected fluid propellant therein to apply a predetermined positive pressure to medication within said medication chamber;

a flow restrictive element, said flow restrictive element having a first end in flow communication with medication within said medication chamber; and an outlet port fitting being coupled in flow communication with a second end of said flow restrictive element for substantially constant delivery of medication passing through said flow restrictive element to a patient wherein said inlet port includes a feedback device that indicates proper engagement with the refill needle.

33. A medication infusion pump, comprising:

a housing formed to define a hollow housing interior, said hollow housing interior forming a medication chamber for receiving a selected medication;

an inlet port mounted on said housing and adapted for removable reception of a refill needle to permit delivery of the medication into said medication chamber, wherein said inlet port includes a feedback device that indicates proper engagement with the refill needle;

a propellant reservoir positioned within said medication chamber said propellant reservoir comprising a sealed flexible bag with a selected fluid propellant therein to apply a predetermined positive pressure to medication within said medication chamber;

a flow restrictive element, said flow restrictive element having a first end in flow communication with medication within said medication chamber; and an outlet port fitting being coupled in flow communication with a second end of said flow restrictive element for delivering medication passing through said flow restrictive element to a patient, wherein said feedback device comprises a click plate positioned within said inlet port for over-center click movement upon proper engagement of said inlet port with the refill needle.

34. A medication infusion pump, comprising:

a housing formed to define a hollow housing interior, said hollow housing interior forming a medication chamber for receiving a selected medication;

an inlet port mounted on said housing and adapted for removable reception of a refill needle to permit delivery of the medication into said medication chamber, wherein said inlet port includes a feedback device that indicates proper engagement with the refill needle;

a propellant reservoir positioned within said medication chamber said propellant reservoir comprising a sealed flexible bag with a selected fluid propellant therein to apply a predetermined positive pressure to medication within said medication chamber;

a flow restrictive element, said flow restrictive element having a first end in flow communication with medication within said medication chamber; and an outlet port fitting being coupled in flow communication with a second end of said flow restrictive element for delivering medication passing through said flow restrictive element to a patient, wherein said inlet port comprises a port body having a valve seat mounted therein, and a valve member movable relative to said valve seat between a closed position and an open position, said valve member being engageable by the refill needle for movement to the open position upon proper engagement of the refill needle with the inlet port, said valve member displacing said feedback device upon movement to the open position to indicate proper engagement between the refill needle and the inlet port.

35. The medication infusion pump of claim 34, wherein said inlet port further includes a spring that biases said valve member to said closed position.

36. The medication infusion pump of claim 34, wherein said feedback device comprises a tactile feedback device.

37. The medication infusion pump of claim 34, wherein said feedback device comprises an audible feedback device.

38. A medication infusion pump, comprising:

a housing defining a hollow interior forming a medication chamber for receiving a selected medication;

a propellant reservoir mounted within said medication chamber, said propellant reservoir comprising a sealed flexible bag having a selected fluid propellant contained therein;

an inlet port mounted on said housing and adapted for removable reception of a refill needle to permit delivery of the selected medication into the interior of said housing, said inlet port preventing a refill needle received therein from contacting said propellant reservoir;

a flow restrictive element having a first end in flow communication with medication contained within said housing interior; and a fitting that connects a second end of said flow restrictive element to a catheter for delivery of the medication to a patient, said propellant reservoir applying a predetermined pressure to the medication within said housing interior to cause the medication to flow at a substantially constant rate through said flow restrictive element, wherein the sealed flexible bag is formed from an upper flexible sheet of material connected to a lower sheet, wherein the sealed flexible bag has a size and shape to conform and substantially entirely fill the medication chamber in the absence of medication within the medication chamber, and wherein the upper flexible sheet of the sealed flexible bag progressively collapses to a reduced volumetric size upon introduction of medication into the medication chamber to a substantially minimum volumetric size permitting substantially all of the medication chamber to be filled with medication.

39. The medication infusion pump of claim 38 wherein said flow restrictive element comprises an elongated capillary tube.

40. The medication infusion pump of claim 39 wherein said capillary tube is coiled generally at the perimeter of said housing interior.

41. The medication infusion pump of claim 40 wherein said capillary tube comprises a glass-based capillary tube.

42. The medication infusion pump of claim 41 wherein said capillary tube comprises a plastic coated glass tube.

43. The medication infusion pump of claim 39, further including a mounting for said capillary tube generally at the perimeter of said housing interior.

44. The medication infusion pump of claim 43, wherein said mounting further includes a filter mounted at said first end of said capillary tube for filtering medication flowing into said capillary tube from said housing interior.

45. The medication infusion pump of claim 44, wherein said mounting directs medication flow from said medication chamber through said filter and into said capillary tube.

46. The medication infusion pump of claim 45, wherein said filter has a generally annular shape to extend generally about the perimeter of said housing interior and oriented for radially outward flow of medication through said filter and into said first end of said capillary tube.

47. The medication infusion pump of claim 38 wherein said selected fluid propellant is a mixed liquid-vapor phase fluid at normal body temperature and ambient pressure conditions to apply said predetermined pressure to the medication within said housing interior.

48. The medication infusion pump of claim 38, wherein said inlet port includes a feedback device that indicates proper engagement with the refill needle.

49. A medication infusion pump, comprising:

a housing defining a hollow interior forming a medication chamber for receiving a selected medication;

a propellant reservoir mounted within said medication chamber, said propellant reservoir comprising a sealed flexible bag having a selected fluid propellant contained therein;

an inlet port mounted on said housing and adapted for removable reception of a refill needle to permit delivery of the selected medication into the interior of said housing, said inlet port preventing a refill needle received therein from contacting said propellant reservoir;

a flow restrictive element having a first end in flow communication with medication contained within said housing interior, wherein said flow restrictive element comprises an elongated capillary tube;

a fitting that connects a second end of said flow restrictive element to a catheter for delivery of the medication to a patient, said propellant reservoir applying a predetermined pressure to the medication within said housing interior to cause the medication to flow through said flow restrictive element; and a bobbin assembly mounted within said housing interior generally at the perimeter thereof, said bobbin assembly including an annular filter element extending generally around the perimeter of said housing interior for radial outflow passage of medication through said filter element to said capillary tube.

50. The medication infusion pump of claim 49 wherein said bobbin assembly comprises a perforated inner bobbin ring and an outer bobbin ring assembled in generally concentric relation with said annular filter element disposed therebetween, said outer bobbin ring having a flow port formed therein with said one end of said capillary tube connected thereto.

51. The medication infusion pump of claim 50 wherein said outer bobbin ring further includes an outer surface defining a shallow circumferential recess for spooled reception of said capillary tube therein.

52. The medication infusion pump of claim 50, wherein said bobbin assembly further includes a seal for preventing bypass flow of medication around said filter element.

53. The medication infusion pump of claim 50, wherein said propellant reservoir has an outwardly extending flange formed thereon, said flange being disposed between said bobbin assembly and said housing such that said bobbin assembly retains said propellant reservoir in place within said housing.

54. The medication infusion pump of claim 53 wherein said capillary tube is coiled within said housing.

55. A medication infusion pump, comprising:

a housing defining a hollow interior foaling a medication chamber for receiving a selected medication;

a propellant reservoir mounted within said medication chamber, said propellant reservoir having a selected fluid propellant therein to apply a predetermined pressure to medication within said medication chamber;

an inlet port mounted on said housing and adapted for removable reception of a refill needle to permit delivery of the selected medication into the medication chamber;

an annular filter element including a support member to support said filter element within said housing generally at the perimeter of said medication chamber and in flow communication with the medication within the medication chamber such that the predetermined pressure applied to the medication by said propellant reservoir causes the medication to flow radially outwardly through said filter element;

a flow restrictive element mounted having a fist end in flow communication with medication passing through said filter element; and a fitting that connects a second end of said flow restrictive element to a catheter for substantially constant delivery of the medication to a patient, wherein the propellant reservoir is formed from an upper flexible sheet of material connected to a lower sheet, wherein the propellant reservoir has a size and shape to conform and substantially entirely fill the medication chamber in the absence of medication within the medication chamber, and wherein the upper flexible sheet of the propellant reservoir progressively collapses to a reduced volumetric size upon introduction of medication into the medication chamber to a substantially minimum volumetric size permitting substantially all of the medication chamber to be filled with medication.

56. The medication infusion pump of claim 55 wherein said flow restrictive element is mounted within said housing.

57. The medication infusion pump of claim 55 wherein said flow restrictive element comprises an elongated capillary tube.

58. The medication infusion pump of claim 57 wherein said capillary tube is coiled within said housing generally at the perimeter thereof.

59. The medication infusion pump of claim 57 wherein said capillary tube comprises a glass-based capillary tube.

60. The medication infusion pump of claim 59 wherein said capillary tube comprises a plastic coated glass tube.

61. The medication infusion pump of claim 55, wherein said inlet port includes a feedback device that indicates proper engagement with the refill needle.

62. A medication infusion pump, comprising:

a housing defining a hollow interior forming a medication chamber for receiving a selected medication;

a propellant reservoir mounted within said medication chamber, said propellant reservoir having a selected fluid propellant therein to apply a predetermined pressure to medication within said medication chamber;

an inlet port mounted on said housing and adapted for removable reception of a refill needle to permit delivery of the selected medication into the medication chamber;

an annular filter element including a support member to support said filter element within said housing generally at the perimeter of said medication chamber and in flow communication with the medication within the medication chamber such that the predetermined pressure applied to the medication by said propellant reservoir causes the medication to flow radially outwardly through said filter element;

a flow restrictive element mounted having a first end in flow communication with medication passing through said filter element; and a fitting that connects a second end of said flow restrictive element to a catheter for delivery of the medication to a patient, wherein said support for said filter element comprises a bobbin assembly having a perforated inner bobbin ring and an outer bobbin ring assembled in generally concentric relation with said annular filter element disposed therebetween.

63. The medication infusion pump of claim 62 wherein said outer bobbin ring has a flow port formed therein with said first end of said capillary tube connected thereto.

64. The medication infusion pump of claim 63 wherein said outer bobbin ring includes an outer surface defining a shallow circumferential recess for spooled reception of said capillary tube therein.

65. A medication infusion pump, comprising:

a housing defining a hollow interior forming a medication chamber for receiving a supply of a selected medication;

a propellant reservoir mounted within said medication chamber, said propellant reservoir comprising a sealed flexible bag having a selected fluid propellant therein to apply a predetermined pressure to medication within said medication chamber;

an inlet port mounted on said housing and adapted for removable reception of a refill needle to permit refilling of the medication chamber with the selected medication;

a bobbin assembly mounted within said housing generally at the perimeter of said housing interior, said bobbin assembly including an annular filter element extending generally around the perimeter of said medication chamber for radial outflow passage of medication from said medication chamber through said filter element, and an elongated capillary tube having one end in flow communication with said filter element for metered flow of the medication passing through said filter; and fitting means for connecting an opposite end of said capillary tube to a catheter for delivery of the medication to a patient.

66. The medication infusion pump of claim 65 wherein said propellant reservoir is filled with said selected propellant to apply a positive pressure to the medication within said medication chamber.

67. The medication infusion pump of claim 65 wherein said capillary tube comprises a glass-based capillary tube.

68. The medication infusion pump of claim 67 wherein said capillary tube comprises a plastic coated glass capillary tube.

69. The medication infusion pump of claim 65 wherein said bobbin assembly comprises a perforated inner bobbin ring and an outer bobbin ring assembled in generally concentric relation with said annular filter element disposed therebetween, said outer bobbin ring having a flow port formed therein with said one end of said capillary tube connected thereto.

70. The medication infusion pump of claim 69 wherein said outer bobbin ring further includes an outer surface defining a shallow circumferential recess for spooled reception of said capillary tube therein.

71. The medication infusion pump of claim 69 wherein said bobbin assembly further includes seal means for preventing bypass flow of medication around said filter element.

72. The medication infusion pump of claim 69 wherein said propellant reservoir bag has an outwardly extending flange formed thereon, said bag flange being disposed beneath said bobbin assembly when said propellant reservoir and said bobbin assembly are mounted into said housing, whereby said bobbin assembly retains said propellant reservoir in place within said housing.

73. The medication infusion pump of claim 65 wherein said inlet port includes feedback means for indicating proper engagement with the refill needle.

74. A medication infusion pump, comprising:

a housing having a medication chamber therein for receiving a supply of a selected medication;

a flexible pressure reservoir mounted within said medication chamber in a position to apply a selected positive pressure to medication within said medication chamber;

an inlet port mounted on said housing and adapted to receive a refill needle to permit refilling of the medication chamber with the selected medication;

a bobbin assembly of generally circular shape mounted into said housing generally at a perimeter of said medication chamber, said bobbin assembly including a perforated inner bobbin ring mounted in concentric relation with an outer bobbin ring having an outlet port formed therein, a generally annular filter element interposed between said inner and outer bobbin rings, and a capillary tube having one end connected to said outlet port in said outer bobbin ring and being spooled about said outer bobbin ring; and fitting means for connecting an opposite end of said capillary tube to a catheter for delivery of medication passing from the medication chamber and through said inner bobbin ring and filter element and capillary tube to a patient.

75. The medication infusion pump of claim 74 wherein said capillary tube is a glass-based capillary tube.

76. The medication infusion pump of claim 74 wherein said filter element is secured to one of said inner and outer bobbin rings.

77. The medication infusion pump of claim 74 wherein said outer bobbin ring further includes an outer surface defining a shallow circumferential recess for spooled reception of said capillary tube therein.

78. The medication infusion pump of claim 74 wherein said bobbin assembly further includes seal means for preventing bypass flow of medication around said filter element.

79. The medication infusion pump of claim 74 wherein said pressure reservoir includes an outwardly extending flange formed thereon, said flange being disposed beneath said bobbin assembly when said pressure reservoir and said bobbin assembly are mounted into said housing, whereby said bobbin assembly retains said pressure reservoir in place within said housing.

80. The medication infusion pump of claim 74 wherein said inlet port include feedback means for indicating proper engagement with the refill needle.

81. The medication infusion pump of claim 74 wherein said fitting means comprises a side port fitting mounted onto said housing, said fitting means having said catheter connected thereto.

82. The medication infusion pump of claim 74 wherein said bobbin assembly has a flat segment formed therein for clearance relative to said fitting means when said bobbin assembly is mounted into said housing.

83. A medication infusion pump, comprising:

a housing defined by a pair of interfitting first and second shell-shaped housing elements;

a pressure reservoir including a flexible sealed bag with a selected propellant therein slide-fitted into said first housing element, said sealed bag having an outwardly extending flange thereon;

a bobbin assembly slide-fitted into said first housing element in seated relation on said bag flange to retain said pressure reservoir in place, said bobbin assembly including a perforated inner bobbin ring mounted in concentric relation with an outer bobbin ring having an outlet port formed therein, a generally annular filter element interposed between said inner and outer bobbin rings, and a capillary tube having one end connected to said outlet port in said outer bobbin ring and being spooled about said outer bobbin ring;

fitting means for connecting an opposite end of said capillary tube to a catheter for delivery of medication to a patient;

means for connecting said first and second housing elements in hermetically sealed relation to form said housing with a hollow interior defining a medication chamber, with said pressure reservoir occupying a portion of said medication chamber, and wherein the balance of said medication chamber is available for receiving a selected medication; and an inlet port mounted adapted to receive a refill needle to permit refilling of the medication chamber with the selected medication;

said pressure reservoir applying a selected pressure to medication within said medication chamber to cause the medication to flow through said inner bobbin ring and said filter element and further through said capillary tube and catheter for delivery to the patient.

84. An inlet port for a medication infusion pump, said inlet port comprising:

a port body having a needle access port formed therein for receiving a refill needle;

a resilient septum supported on said port body for piercing by the refill needle upon passage of the refill needle through said needle access port;

a valve seat within said port body;

a valve member mounted within said port body for movement between a closed position engaging said valve seat and an open position spaced from said valve seat, said valve member being engageable by the refill needle upon passage thereof through said needle access port to move said valve member to the open position, wherein said port body includes a hard stop to prevent said valve member from moving past the open position; and A feedback device carried by said port body, in addition to said hard stop, and said feedback device being activated by said valve member upon movement to said open position to indicate proper engagement between said valve member and the refill needle.

85. The inlet port of claim 84, further including a spring that biases said valve member normally to said closed position.

86. The inlet port of claim 84, wherein said feedback device comprises a tactile feedback device.

87. An inlet port for a medication infusion pump, said inlet port comprising:

a port body having a needle access port formed therein for receiving a refill needle;

a resilient septum supported on said port body for piercing by the refill needle upon passage of the refill needle through said needle access port;

a valve seat within said port body;

a valve member mounted within said port body for movement between a closed position engaging said valve seat and an open position spaced from said valve seat, said valve member being engageable by the refill needle upon passage thereof through said needle access port to move said valve member to the open position; and a feedback device carried by said port body and displaced by said valve member upon movement to said open position to indicate proper engagement between said valve member and the refill needle.

wherein said feedback device comprises a click plate positioned within said port body for over-center click movement upon displacement thereof by said valve member.

88. An inlet port for a medication infusion pump, said inlet port comprising:

a port body having a needle access port formed therein for receiving a refill needle;

a resilient septum supported on said port body for piercing by the refill needle upon passage of the refill needle through said needle access port;

a valve seat within said port body;

a valve member mounted within said port body for movement between a closed position engaging said valve seat and an open position spaced from said valve seat, said valve member being engageable by the refill needle upon passage thereof through said needle access port to move said valve member to the open position; and a feedback device carried by said port body and displaced by said valve member upon movement to said open position to indicate proper engagement between said valve member and the refill needle, wherein said feedback device comprises an audible feedback device.

89. An inlet port for a medication infusion pump, said inlet port comprising:

a port body having a needle access port formed therein for receiving a refill needle;

a resilient septum supported on said port body for piercing by the refill needle upon passage of the refill needle through said needle access port;

a valve seat within said port body;

a valve member mounted within said port body for movement between a closed position engaging said valve seat and an open position spaced from said valve seat, said valve member being engageable by the refill needle upon passage thereof through said needle access port to move said valve member to the open position;

a feedback device carried by said port body and displaced by said valve member upon movement to said open position to indicate proper engagement between said valve member and the refill needle;

a spring that biases said valve member normally to said closed position: and a plug member adjustably mounted to said port body, said spring reacting between said valve member and said plug member, and said feedback device being disposed between said valve member and said plug member.

90. The inlet port of claim 89 further including a filter element carried by said plug member for filtering medication delivered through said port body by said refill needle.

91. A medication infusion pump, comprising:

a housing formed to define a hollow housing interior, said hollow housing interior forming a propellant chamber for receiving a selected fluid propellant to apply a predetermined positive pressure;

a medication reservoir positioned within the propellant chamber, the medication reservoir comprising a sealed flexible bag to receive a selected medication, to apply the predetermined positive pressure of the selected fluid propellant in the propellant chamber to the medication reservoir;

an inlet port mounted on said housing and adapted for removable reception of a refill needle to permit delivery of the medication into the medication reservoir;

a flow restrictive element, the flow restrictive element having a first end in flow communication with medication within the medication reservoir; and an outlet port fitting being coupled in flow communication with a second end of the flow restrictive element for substantially constant delivery of medication passing through the flow restrictive element to a patient, wherein the sealed flexible bar is formed from an upper flexible sheet of material connected to a lower sheet, wherein the sealed flexible bag has a size and shape to conform and substantially entirely fill the propellant chamber in the presence of medication within the sealed flexible bag, and wherein the upper per flexible sheet of the sealed flexible bar progressively collapses to a reduced volumetric size upon expulsion of medication from the sealed flexible bag to a substantially minimum volumetric size permitting substantially all of the propellant chamber to be filled will propellant.

92. A substantially constant flow medication infusion pump, comprising:

a horsing formed to define a hollow housing interior, said hollow housing interior forming a medication chamber for receiving a selected medication;

an inlet port mounted on said housing and adapted for removable reception of a refill needle to permit delivery of the medication into said medication chamber, wherein said inlet port comprises a port body having a valve seat mounted therein, and a valve member movable relative to said valve seat between a closed position and an open position, said valve member being engageable by the refill needle for movement to the open position upon proper engagement of the refill needle with the inlet port, and wherein said inlet port includes a resilient septum supported on said port body for piercing by the refill needle upon passage of the refill needle through said needle access port;

a propellant reservoir positioned within said medication chamber, said propellant reservoir comprising a sealed flexible bag with a selected fluid propellant therein to apply a predetermined positive pressure to medication within said medication chamber;

a flow restrictive element, said flow restrictive element having a first end in substantially constant flow communication with medication within said medication chamber; and an outlet port fitting being coupled in substantially constant flow communication with a second end of said flow restrictive element for substantially constant delivery of medication passing through said flow restrictive element to a patient, wherein the sealed flexible bay is formed from an upper flexible sheet of material connected to a lower sheet, wherein the sealed flexible bag has a size and share to con form and substantially entirely fill the medication chamber in the absence of medication within the medication chamber, and wherein the upper flexible sheet of the sealed flexible bag progressively collapses to a reduced volumetric size upon introduction of medication into the medication chamber to a substantially minimum volumetric size permitting substantially all of the medication chamber to be filled with medication.

* * * * *